(12) United States Patent
Scialdone

(10) Patent No.: US 8,748,477 B2
(45) Date of Patent: Jun. 10, 2014

(54) FORMULATIONS CONTAINING INSECT REPELLENT COMPOUNDS

(75) Inventor: Mark A. Scialdone, West Grove, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1154 days.

(21) Appl. No.: 11/266,641

(22) Filed: Nov. 3, 2005

(65) Prior Publication Data

US 2006/0223878 A1 Oct. 5, 2006

Related U.S. Application Data

(60) Provisional application No. 60/624,579, filed on Nov. 3, 2004.

(51) Int. Cl.
*A01N 25/00* (2006.01)
*A61K 8/34* (2006.01)
*A01N 43/16* (2006.01)

(52) U.S. Cl.
CPC ..................................... *A01N 43/16* (2013.01)
USPC ............. 514/427; 424/405; 424/59; 514/617

(58) Field of Classification Search
CPC ...................................................... A01N 43/16
USPC ............ 514/457, 918, 617, 427, 456; 424/45, 424/405, 401, 408; 43/132
See application file for complete search history.

(56) References Cited

U.S. PATENT DOCUMENTS

| | | | | |
|---|---|---|---|---|
| 4,062,937 | A | * | 12/1977 | Rea .................................. 424/47 |
| 4,416,881 | A | | 11/1983 | McGovern et al. |
| 4,469,613 | A | | 9/1984 | Munteanu et al. |
| 4,476,147 | A | * | 10/1984 | Hall et al. ...................... 426/534 |
| 4,496,467 | A | | 1/1985 | Munteanu et al. |
| 4,548,764 | A | | 10/1985 | Munteanu et al. |
| 4,663,346 | A | | 5/1987 | Coulston et al. |
| 4,869,896 | A | | 9/1989 | Coulston et al. |
| 4,913,893 | A | * | 4/1990 | Varco et al. ..................... 424/47 |
| 6,013,255 | A | | 1/2000 | Edens |
| 6,524,605 | B1 | | 2/2003 | Coats |
| 6,623,694 | B1 | * | 9/2003 | Ferguson et al. ................. 422/5 |
| 6,673,756 | B2 | | 1/2004 | Sonnenberg |
| 7,067,677 | B2 | | 6/2006 | Manzer |
| 7,067,678 | B2 | | 6/2006 | Scialdone |
| 7,232,844 | B2 | | 6/2007 | Hallahan |
| 7,250,174 | B2 | | 7/2007 | Lee |
| 7,435,851 | B2 | | 10/2008 | Scialdone |
| 7,820,145 | B2 | | 10/2010 | Tamarkin |
| 2001/0009925 | A1 | * | 7/2001 | Lambino et al. ............. 514/613 |
| 2002/0173436 | A1 | * | 11/2002 | Sonnenberg et al. ......... 510/141 |
| 2003/0062357 | A1 | | 4/2003 | Schneider et al. |
| 2003/0079786 | A1 | | 5/2003 | Diana et al. |
| 2003/0191047 | A1 | * | 10/2003 | Hallahan ........................ 512/13 |
| 2004/0028629 | A1 | * | 2/2004 | Cai et al. ........................ 424/65 |
| 2004/0127553 | A1 | | 7/2004 | Hallahan |
| 2005/0137252 | A1 | | 6/2005 | Scialdone |
| 2005/0239875 | A1 | | 10/2005 | Scialdone |
| 2005/0244441 | A1 | * | 11/2005 | Courtois et al. .............. 424/401 |
| 2006/0148842 | A1 | | 7/2006 | Scialdone |
| 2006/0201391 | A1 | | 9/2006 | Scialdone |
| 2006/0228387 | A1 | | 10/2006 | Scialdone |
| 2007/0077262 | A1 | | 4/2007 | Scialdone |
| 2007/0264297 | A1 | | 11/2007 | Scialdone |

FOREIGN PATENT DOCUMENTS

| | | |
|---|---|---|
| EP | 1997382 | 12/2008 |
| WO | WO 95/28092 | * 10/1995 |
| WO | WO 03/084946 A1 | 10/2003 |
| WO | WO 2005/034626 | 4/2005 |

OTHER PUBLICATIONS

U.S. Appl. No. 10/349,865, filed Jan. 23, 2003, David L. Hallahan.
Nedjalka V. Handjieva et al., Constituents of Essential Oils From Nepeta Cataria L., N. Grandiflora M.B. and N. Nuda L., J. Essent. Oil Res., vol. 8:639-643, 1996.
Shinji Tanimori et al., Total Synthesis of (+−)-Dihydronepetalactone, Agric. Biol. Chem., vol. 55(4):1181-1183, 1991.
Matthew M. Abelman et al., Alicyclic Claisen Rearrangement. A General Carbocycle Synthesis is based on Four-Atom-Ring Contractions of Lactones, J. Am. Chem. Soc., vol. 104:4030-4032, 1982.
J. Wolinksy et al., The Synthesis of (+)-Matatabiether and Related Methylcyclopentane Monoterpenes, Tetrahdron, vol. 25:3767-3774, 1969.
Joseph Wolinsky et al., Synthesis of the Dihydronepetalactones, J. Org. Chem., vol. 37(21):3376-3378, 1972.
Tadao Uyehara et al., New Type of Cyclization of A,B,X,Y-Unsaturated Dioic Acid Esters Through Tandem Conjugate Additions by Using Lithium N-Benzyl-N-(Trimethylsily)Amide as a Nitrogen Nucleophile, J. Org. Chem., vol. 57:3139-3145, 1992.
A. Nangia et al., Intramolecular Horner-Wadsworth-Emmons Reaction in Base Sensitive Substrates: Enantiospecific Synthesis of Iridoid Monoterpene Lactones, Tetrahedron Letters, vol. 35:(22):3755-3758, 1994.
G. W. K. Cavill et al., Defensive and Other Secretions of the Australian Cocktail Ant, Iridomyrmex Nitidiceps, Tetrahedron, vol. 38(13):1931-1938, 1982.
G. W. K. Cavill et al., Insect Venoms, Attractants, and Repellents-VIII. Isodihydronepetalactone, J. Insect Physiol., vol. 13:131-135, 1987.
Igor I. Pottosin et al., Slowly Activating Vacuolar Channels Can Not Mediate CA2+-Induced CA2+ Release, The Plant Journal, vol. 12(6):1387-1398, 1997.
F. E. Regnier et al., Studies on the Composition of the Essential Oils of Three Nepeta Species*, Phytochemistry, vol. 6:1281-1289, 1967.
The Condensed Chemical Dictionary, Edition 8, p. 756-757.

(Continued)

*Primary Examiner* — Richard Schnizer
*Assistant Examiner* — Yanzhi Zhang

(57) ABSTRACT

Dihydronepetalactone, a minor natural constituent of the essential oil of catmints (*Nepeta* spp.) such as *Nepeta cataria*, has been identified as an effective insect repellent compound. Synthesis of dihydronepetalactone may be achieved by hydrogenation of nepetalactone, the major constituent of catmint essential oils. This compound, and compositions thereof, which also has fragrance properties, may be used commercially for its insect repellent properties.

9 Claims, 1 Drawing Sheet

(56) References Cited

OTHER PUBLICATIONS

Hay, R.K.M. et al., Botany, In "Volatile Oil Crops: Their Biology, Chemistry and Production", Hay, R.K.M. Edition; Longman Group UK Limited , 1993.

Thomas Eisner, Defensive Spray of a Phasmid Insect, Science, vol. 148:966-968, 1965.

Ian Fleming et al., Stereocontrol in Organic Synthesis Using Silicon-Containing Compounds. A Synthesis of (+−)-Dihydronepetalactone using the SE2' Reaction of an Allylsilane, J. Chem. Soc., Perkin Trans., vol. 1:2645-2650, 1998.

Tennen Yuki Kagobutsu Toronkai Koen Yoshishu, vol. 32:441-446, 1990.

G. Briassoulis et al., Toxic Encephalopathy Associated With Use of Deet Insect Repellents: A Case Analysis of its Toxicity in Children, Human & Experimental Toxicology, vol. 20:8-14, 2001.

Ian Fleming et al., Stereospecific Allylsilane Reactions: A Total Synthesis of Dihydronepetalactone, Tetrahedron Letters, vol. 25(44):5103-5104, 1984.

Kirk-Othmer Encyclopedia of Chemical Technology, Edition 2, vol. 11, pp. 724-728.

Chris Peterson et al., Insecticidal Activity of Cyanohydrins and Their Qsar., Abstracts of Papers, ACS, vol. 222, 2001.

The Condensed Chemical Dictionary, Edition 8, p. 756-757, published 1928.

Hay, R.K.M. et al., Botany, In "Volatile Oil Crops: Their Biology, Chemistry and Production", Hay, R.K.M. Edition, Longman Group UK Limited, 1993 (Book Not Supplied).

Tadao Uyehara et al., Cyclisation of A,B,X,U-Unsaturated Dioic Acid Esters via Tandem Conjugate Additions by Using Lithium N-Benzyltrimethylsilylamide (LSA) as a Nitrogen Nucleophile and Its Application to a Total Synthesis of (+−)-Dihydronepetalactone and (+_)-Isodihydronepetalactone, J. Chem. Soc., Chem. Commun., vol. 2:113-114, 1989.

Eun Lee et al., Stereoselective Favorskii Rearrangement of Carvone Chlorohydrin; Expedient Synthesis of (+)-Dihydronepetalactone and (+)-Iridomyrmecin, vol. 4:479-481, 1994.

Thomas Eidner, Defense Spray of a Phasmid Insect, Science, vol. 148:966-968, 1965.

Ian Fleming et al., Stereocontrol in Organic Synthesis Using Silicon-Containing Componds. A Synthesis of (+−)-Dihydronepetalactone Using the SE2' Reaction of an Allylsilane, J. Chem. Soc., Perkin Trans., vol. 1:2645-2650, 1998.

Tennen Yuki Kahobutsu Toronkai Koen Yoshishu, vol. 32:441-446, 1990.

H. L. de Pooter et al., The Essential Oils of Five Nepeta Species. A Preliminary Evaluation of Their Use in Chemotaxonomy by Cluster Analysis*, Flavour and Fragrance Journal, vol. 3:155-159, 1988.

Martin Jefson et al., Chemical Defense of a Rove Beetle, Journal of Chemical Ecology, vol. 9(1):159-180, 1983.

Mark S. Fradin et al., Comparative Efficacy of Insect Repellents Against Mosquito Bites, N Engl. J. Med., vol. 347(1):13-18, 2002.

G. Briassoulis et al., Toxic Encepthalopathy Associated With Use of Deet Insect Repellents: A Case Analysis of Its Toxicity in Children, Human & Experimental Toxicology, vol. 20:8-14, 2001.

Ian Fleming et al., Stereospecific Allylsilane Reactions: A Total Synthesis of Dihydronepetalactone, Tetrahedron Letters, vol. 25(44):5103-4104, 1984.

Hiroshi Nagata et al., Concurrent Resolution and Oxidation of an Allylic Acetate and Its Utilization in the Diastereocontrolled Synthesis of Some Cyclopentanoid Monoterpenes, Tetrahedron Letters, vol. 40:6617-6620, 1999.

Kirk-Othmer Encyclopedia of Chemical Technology, Edition 2, vol. 11, pp. 724-728, Mar. 9, 2003

Chris Peterson et al., Insecticidal Activity of Cyanohydrins and Their QSAR, Abstracts of Papers, ACS, vol. 222, 2001.

Thomas Eisner, Catnip: Its Raison d'Etre, Science, vol. 146:1318-1320, 1964.

Chris Peterson et al., Insect Repellents—Past, Present and Future, Pesticide Outlook, p. 154-158, 2001.

G. Schultz et al., Natural Insect Repellents: Activity Against Mosquitoes and Cockroaches, ACS Symposium Series, 2006, vol. 927:168-181.

Edmund J. Eisenbraun et al., (4AS, 7S, 7AR)-Nepetalactam and (4AS,7S,7AR)-2-[(3R,4R,4AR,7S,7AR)-Octahydro-4,7-Dimethyl-1-Oxocyclopenta[C]pyran-3-Yi]Nepetalactam: Nitrogen Analogues of Nepatalactone and Nepetalic-Anhydride, J. Org. Chem., vol. 53-3968-3972, 1988.

International Search Report and Written Opinion in PCT/US2005/040146, Nov. 3, 2005.

* cited by examiner

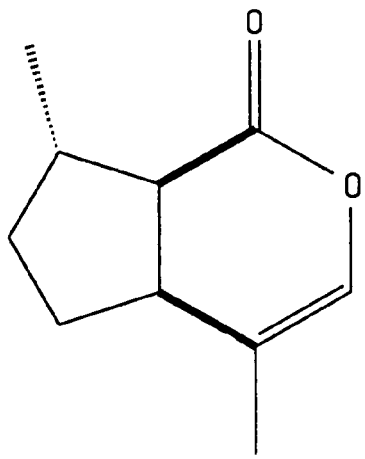
(4a,7S,7aR) nepetalactone
(cis, trans-nepetalactone)
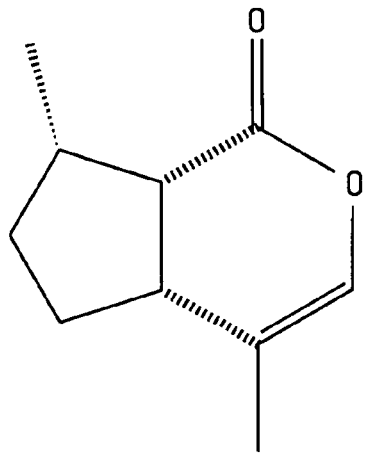
(4a,7S,7aR) nepetalactone
(cis, cis-nepetalactone)
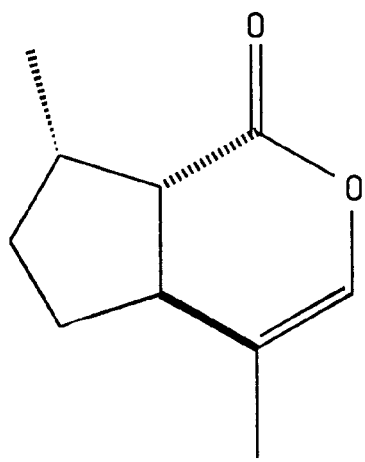
(4a,7S,7aR) nepetalactone
(trans, cis-nepetalactone)
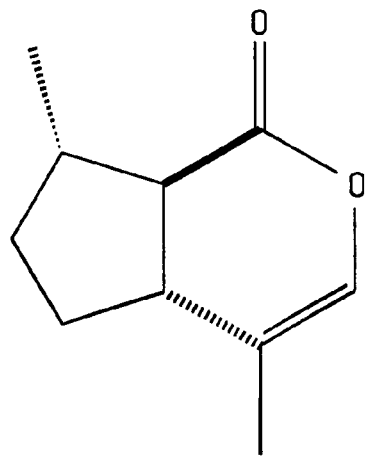
(4a,7S,7aR) nepetalactone
(trans, trans-nepetalactone)

FORMULATIONS CONTAINING INSECT REPELLENT COMPOUNDS

This application claims the benefit of U.S. Provisional Application No. 60/624,579, filed on Nov. 3, 2004, which is incorporated in its entirety as a part hereof for all purposes.

TECHNICAL FIELD

The present invention relates to the field of insect repellency, and the use of dihydronepetalactone stereoisomers generally as repellent materials.

BACKGROUND

Repellent substances generally cause insects to be driven away from, or to reject, otherwise insect-acceptable food sources or habitats. Most known repellents are only mildly toxic. A few of the known repellents, in fact, are not active poisons at all but rather prevent damage to plants/animals or articles of manufacture by making insect food sources or living conditions unattractive or offensive. Most current commercial insect repellents contain the synthetic chemical N,N-diethyl-m-toluamide (DEET) as their primary active ingredient. For instance, repellents sold under the major commercial brand names such as Off!®, Deep Woods Off!®, and Cutter® are all DEET based products and comprise 85% of insect repellent sales (Consumer Reports Buying Guide, 1994 Special Year-End Issue). Further, Consumer Reports tests indicated that products with the highest concentration of DEET lasted the longest against mosquitoes.

Despite being an effective repellent, however, this compound has certain drawbacks. Specifically, it possesses an unpleasant odor and imparts a greasy feel to the skin. Although it has recently been re-registered for use in the US by the EPA, concerns have been raised as to its safety, particularly when applied to children [Briassoulis, G.; Narlioglou, M.; Hatzis, T. (2001) *Human & Experimental Toxicology* 20(1), 8-14]. Studies have demonstrated that high concentrations of DEET may give rise to allergic or toxic reactions in some individuals. Other disadvantages associated with DEET include that it (1) is a synthetic chemical having a limited spectrum of activity; (2) is a powerful plasticizer and will dissolve or mar many plastics and painted surfaces; and (3) plasticizes the inert ingredients typically used in topical formulations in order to lengthen the time of effectiveness. This leads to DEET formulations with low user acceptability.

As a result of the above limitations, DEET-free products with repellent activity are finding favor with consumers, and demand for compositions containing natural products (versus synthetic chemicals such as DEET) is increasing. These DEET-free repellent compounds require a combination of excellent repellency, high residual activity and relatively little or no toxicity to humans (or pets) and the environment. In response to these consumer demands, there is an on-going need to develop new repellent compounds, which can be obtained from, or synthesized from, natural plant materials and which are pleasant to use.

Many plant species produce essential oils (aromatic oils) that are used as natural sources of insect repellent and fragrant chemicals [Hay, R. K. M., Svoboda, K. P., *Botany*, in "Volatile Oil Crops: their biology, chemistry and production"; Hay, R. K. M., Waterman, P. G. (eds.); Longman Group UK Limited (1993)]. Citronella oil, known for its general repellence towards insects, is obtained from the graminaceous plants *Cymbopogon winterianus* and *C. nardus*. Examples of plants used as sources of fragrant chemicals include *Melissa officinalis* (Melissa), *Perilla frutescens* (Perilla), *Posostemon cablin* (Patchouli) and various *Lavandula* spp. (Lavender). All of these examples of plants yielding oil of value to the fragrance industry are members of the Labiatae (Lamiaceae) family. Plants of the genus *Nepeta* (catmints) are also members of this family, and produce an essential oil, which is a minor item of commerce. This oil is very rich in a class of monoterpenoid compounds known as iridoids [Inouye, H. *Iridoids. Methods in Plant Biochemistry* 7:99-143 (1991)], more specifically the methylcyclopentanoid nepetalactones [Clark, L. J. et al. *The Plant Journal*, 11:1387-1393 (1997)] and derivatives.

Iridoid monoterpenoids have long been known to be effective repellents to a variety of insect species [Eisner, T. *Science* 146:1318-1320 (1964); Eisner, T. *Science* 148:966-968 (1965); Peterson, C. and J. Coats, *Pesticide Outlook* 12:154-158 (2001); and Peterson, C. et al. *Abstracts of Papers American Chemical Society*, (2001) 222 (1-2): AGRO73]. U.S. Pat. No. 4,663,346 discloses insect repellants with compositions containing bicyclic iridoid lactones (e.g., iridomyrmecin). Further, U.S. Pat. No. 4,869,896 discloses use of these bicyclic iridoid lactone compositions in potentiated insect repellent mixtures with DEET.

Formal studies concerning the repellency of dihydronepetalactones, a class of iridoid monoterpenoids derived from nepetalactones (shown in FIG. 1), have been much less conclusive and have failed to teach or imply that these compounds exert a repellent effect on the common insect pests of human society. For example, a study of the composition of the secretion from anal glands of the ant *Iridomyrmex nitidus* showed that isodihydronepetalactone was present in appreciable amounts, together with isoiridomyrmecin [Cavill, G. W. K., and D. V. Clark. *J. Insect Physiol.* 13:131-135 (1967)]. Although isoiridomyrmecin was known at the time to possess good 'knockdown' insecticidal activity, no evidence was provided in support of a similar activity for isodihydronepetalactone, and no investigation of this compound's repellent effect (as distinct from insecticidal activity) was made.

In a later publication by Cavill, G. W. K., et al. [*Tetrahedron* 38:1931-1938 (1982)], the presence of dihydronepetalactones in the defensive secretion of an ant was again reported, but the authors concluded that the compound iridodial, rather than a dihydronepetalactone, was the basic repellent constituent.

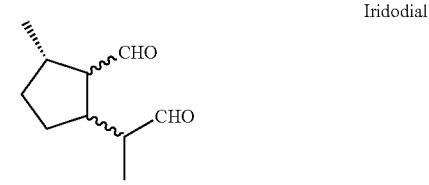

Iridodial

Most recently, Jefson, M., et al. [*J. Chemical Ecology* 9:159-180 (1983)] described the repellent effect of dihydronepetalactone. Initial repellency caused by the undiluted compound was measured with respect to the ant species *Monomorium destructor* during feeding. After 25 seconds of exposure to the pure dihydronepetalactone, approximately 50-60% of the ants ceased to feed. However, further analyses of the repellency over a longer time course were not presented, nor were analyses with anything other than the pure undiluted compound. Repellency observed over such short periods of time (seconds) with concentrated chemicals is insufficient to allow prediction of efficacy in practical applications such as in topical insect repellents.

There is consequently a continuing need for a biologically based compound having improved insect repellent properties (with respect to DEET) and which is substantially non-toxic or only mildly toxic to humans. Preferred repellents will have activity against a wide variety of insects, including biting insects, wood-boring insects, noxious insects, household pests, and the like. Applicants have found that dihydronepetalactones, and compositions thereof, perform well as a new class of effective insect repellent compounds without the disadvantageous properties characteristic of prior-art compositions.

SUMMARY

One embodiment of this invention is an insect repellent composition or article that contains a dihydronepetalactone, or a mixture of dihydronepetalactone stereoisomers, represented by the general formula:

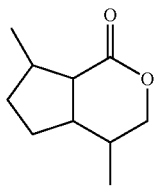

Another embodiment of this invention is a process for fabricating an insect repellent composition or an insect repellent article of manufacture by providing as the composition or article, or incorporating into the composition or article, a dihydronepetalactone, or a mixture of dihydronepetalactone stereoisomers, as described above.

Yet another embodiment of this invention is the use of a dihydronepetalactone, or a mixture of dihydronepetalactone stereoisomers, as described above, or a composition thereof, as an insect repellent; and thus an embodiment in which, in a method of repelling insects, the insects are exposed to a diihydronepetalactone, or a mixture of dihydronepetalactone stereoisomers, or a composition thereof, as described above.

Yet another embodiment of this invention is a formulated inset repellent composition that includes a dihydronepetalactone, or a mixture of dihydronepetalactone stereoisomers, as described above and one or more of a carrier, an adjuvant and an additive.

BRIEF DESCRIPTION OF THE DRAWINGS

FIG. 1 shows the chemical structures of the naturally occurring iridoid (methylcyclopentanoid) nepetalactones.

DETAILED DESCRIPTION

A nepetalactone" is a compound having the general structure:

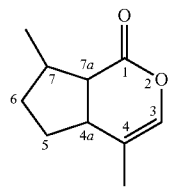

Four chiral centers are present within the methylcyclopentanoid backbone of nepetalactone at carbons 4, 4a, 7 and 7a as shown above; (7S)-nepetalactones are produced by several plants and insects. Dihydronepetalactones are known as minor constituents of the essential oils of several labiate plants of the genus *Nepeta* (Regnier, F. E., et al. (1967) *Phytochemistry* 6:1281-1289; DePooter, H. L., et al. (1988) *Flavour and Fragrance Journal* 3:155-159; Handjieva, N. V. and S. S. Popov (1996) *J. Essential Oil Res.* 8:639-643). Dihydronepetalactones are defined by Formula 1:

Formula I

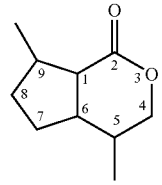

wherein 1, 5, 6 and 9 indicate the four chiral centers of the molecule and the structure encompasses all possible stereoisomers of dihydronepetalactone. The structures of dihydronepetalactone stereoisomers that may be derived from (7S)-nepetalactones are shown below.

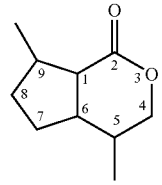

(1S,5S,9S,6R)-5,9-dimethyl-3-oxabicyclo[4.3.0]nonan-2-one

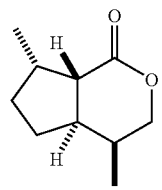

(1S,9S,5R,6R)-5,9-dimethyl-3-oxabicyclo[4.3.0]nonan-2-one

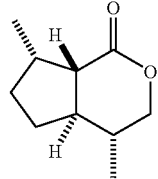

(1S,5S,9S,6S)-5,9-dimethyl-3-oxabicyclo[4.3.0]nonan-2-one

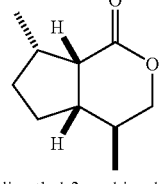

(1S,9S,6S,5R)-5,9-dimethyl-3-oxabicyclo[4.3.0]nonan-2-one

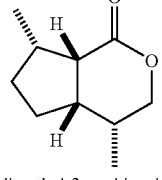

(9S,5S,1R,6R)-5,9-dimethyl-3-oxabicyclo[4.3.0]nonan-2-one

-continued

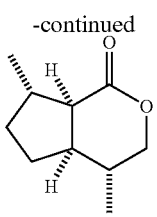

(9S,1R,5R,6R)-5,9-dimethyl-3-oxabicyclo[4.3.0]nonan-2-one

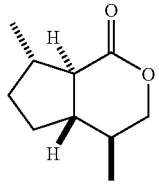

(9S,6S,1R,5S)-5,9-dimethyl-3-oxabicyclo[4.3.0]nonan-2-one

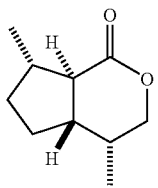

(9S,6S,1R,5R)-5,9-dimethyl-3-oxabicyclo[4.3.0]nonan-2-one

The term "dihydronepetalactones" or "dihydronepetalactone mixtures" refers to any mixture of dihydronepetalactone stereoisomers. The molar or mass composition of each of these isomers relative to the whole dihydronepetalactone composition can be variable. Dihydronepetalactones are abbreviated as "DHN".

A dihydronepetalactone will be understood to encompass any and all dihydronepetalactone stereoisomers and mixtures thereof, unless a particular isomer or mixture is specified. When dihydronepetalactone is prepared from a naturally occurring source of nepetalactone some variation in molar concentration of stereoisomers is expected. Preparation from a naturally occurring source is, however, a preferred method of preparation.

Dihydronepetalactones are reported in the literature as minor constituents of the essential oils of several labiate plants of the genus Nepeta [Regnier, F. E., et al., *Phytochemistry* 6:1281-1289 (1967); DePooter, H. L., et al., *Flavour and Fragrance Journal* 3:155-159 (1988); Handjieva, N. V. and S. S. Popov, *J. Essential Oil Res.* 8:639-643 (1996)]. Additionally, dihydronepetalactones have been identified as constituents of the defensive secretions of certain insects, including rove beetles [Jefson, M., et al., *J. Chem. Ecol.* 9:159-180 (1983)] and ants, specifically Iridomyrmex species [Cavill, G. W. K. and D. V. Clark. *J. Insect Physiol.* 13:131-135 (1967)]. In those species that possess dihydronepetalactones, it has been proposed that they are biosynthetically derived from the iridoid monoterpene iridodial.

The chemical synthesis of dihydronepetalactones and their related iridoid monoterpenoid compounds has been described and found to be conducted in a variety of ways. The following are useful references relating to synthesis:

1) Abelman, M. M. et al. *J. Am. Chem. Soc.* 104 (14):4030-2 (1982)
2) Fleming, I. and N. K. Terrett. *Tetrahedron Lett.* 25(44): 5103-5104 (1984); *J. Chem. Soc., Perkin Trans.* 1:2645-2650 (1998).
3) Lee, E. and C. H. Yoon. *J. Chem. Soc., Chem. Commun.* 4: 479-81 (1994).
4) Nagata, H. and K. Ogasawara. *Tetrahedron Lett.* 40(36): 6617-6620 (1999).
5) Nangia, A. et al. *Tetrahedron Lett.* 35(22): 3755-8 (1994).
6) Tanimori, S. and M. Nakayama. *Agric. Biol. Chem.* 55(4): 1181-1184 (1991).
7) Uyehara, T. et al. *J. Chem. Soc., Chem. Commun.* 2:113-14 (1989); *Tennen Yuki Kagobutsu Toronkai Koen Yoshishu* 32: 441-6 (1990); *J. Org. Chem.* 57(11): 3139-3145 (1992).
8) Wolinsky, J. and E. J. Eustace. *J. Org. Chem.* 37(21): 3376-8 (1972).
9) Wolinsky, J. and D. L. Nelson. *Tetrahedron* 25(17): 3767-74 (1969).

Regnier et al, op.cit., discloses the preparation of DHN from nepetalactone by the catalyzed hydrogenation of nepetalactone isolated from the essential oils of plants of the genus *Nepeta* (catmints). One preferred and convenient method for synthesis of dihydronepetalactone is thus by hydrogenation of nepetalactone obtained in relatively pure form from the essential oils isolated by various means from plants of the genus *Nepeta* (catmints). Catalysts such as platinum oxide and palladium supported on strontium carbonate give dihydronepalactone in 24-90% yields (Regnier et al. op.cit.).

The preferred process for producing the dihydronepetalactones represented by Formula I in the present invention, therefore, is by hydrogenation of nepetalactones from plants with oils of defined nepetalactone stereoisomer content, an industrially advantageous approach in terms of production cost and its biological basis. Other processes are as disclosed in U.S. Ser. No. 03/225,290 (WO 03/84946), which is incorporated in its entirety as a part hereof for all purposes.

Methods for isolation or extraction of essential oils include without limitation steam distillation, organic solvent extraction, microwave-assisted organic solvent extraction, supercritical fluid extraction, mechanical extraction and enfleurage (initial cold extraction into fats followed by organic solvent extraction).

The essential oils isolated from different *Nepeta* species are well known to possess different proportions of each naturally occurring stereoisomer of nepetalactone (Regnier et al. op. cit.; DePooter, et al. op.cit.; Handjieva et al op.cit.). Thus DHN prepared from oil derived from any *Nepeta* species will necessarily be a mixture of stereoisomers thereof, the constitution of that mixture depending upon the particular species of *Nepeta* from which it is derived.

As discussed herein above, four chiral centers are present within the methylcyclopentanoid backbone of the nepetalactone at carbons 4, 4a, 7 and 7a as shown:

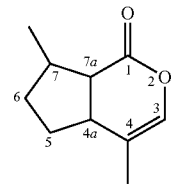

A total of eight pairs of dihydronepetalactone enantiomers are possible after hydrogenation of nepetalactone. Of these, the naturally occurring stereoisomers described thus far are (9S)-dihydronepetalactones. Preferred repellent materials in accordance with the present invention include a mixture of any or all of the possible stereoisomers of dihydronepetalactone. More preferred repellent materials include a mixture of (9S)-dihydronepetalactones. Most preferred are (9S)-dihydronepetalactone stereoisomers derived from (7S)-nepetalactones. This includes the compounds commonly known as cis,trans-nepetalactone, cis,cis-nepetalactone, trans,cis-nepetalactone, and trans,trans-nepetalactone, as illustrated in FIG. 1. The predominant stereoisomers produced by *N. cataria* (cis,trans and trans,cis-) are preferred.

Upon completion of the hydrogenation reaction, the resulting mixture of isomer products may be separated by any conventional method (e.g., preparative liquid chromatography) to yield each highly purified pair of dihydronepetalactone diastereomers. This permits the use of various different diastereomers as are found to be most effective against particular insects. It is preferable to isolate a specific nepetalactone isomer from a plant to convert to its corresponding pair of diastereomers by hydrogenation.

In addition to variation in nepetalactone stereoisomer content between different *Nepeta* species, intra-species variation is also known to exist. Plants of a given species may produce oils with different compositions depending on the conditions of their growth or growth stage at harvest. In fact variation in oil composition independent of growth conditions or growth stage at harvest has been found in *Nepeta racemosa*, (Clark, L. J., et al. op.cit.). Plants of a single species exhibiting different oil compositions are termed chemotypes. In *Nepeta racemosa*, chemotypes exhibiting marked differences in the proportion of different nepetalactone stereoisomers exist. Thus, the preferred process for producing specific dihydronepetalactone enantiomers is hydrogenation of an oil from a *Nepeta* chemotype known to contain specific nepetalactone stereoisomers.

Insects include any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes a variety of biting insects (e.g., ants, bees, black flies, chiggers, fleas, green head flies, mosquitoes, stable flies, ticks, wasps), wood-boring insects (e.g., termites), noxious insects (e.g., houseflies, cockroaches, lice, roaches, wood lice), and household pests (e.g., flour and bean beetles, dust mites, moths, silverfish, weevils).

A host is any plant or animal affected by insects. Typically, hosts are considered to be insect-acceptable food sources or insect-acceptable habitats. An insect susceptible article is any item of commerce created by man, which is affected by insects. This may include buildings, furniture, and the like. Typically, these articles of manufacture are considered to be insect-acceptable food sources or insect-acceptable habitats.

The terms "insect repellent", "insect repellent composition" or "repellent composition" will refer to a compound or composition that deters insects from their preferred hosts or insect-suitable articles of manufacture. Most known repellents are not active poisons at all, but rather prevent damage to plants/animals or articles of manufacture by making insect food sources or living conditions unattractive or offensive. Typically, an insect repellent is a compound or composition that can be either topically applied to the host, or is a compound or composition that may be incorporated into an insect susceptible article to produce an insect repellent article that deters insects from the nearby 3-dimensional space in which the host or article exists. In either case, the effect of the insect repellent is to drive the insects away from or to reject (1) the host, thereby minimizing the frequency of insect "bites" to the host; and/or (2) the insect susceptible article, thereby protecting the article from insect damage. Repellents may be in the form of gases (olfactory), liquids, or solids (gustatory).

Some examples of well-known insect repellents include: benzil; benzyl benzoate; 2,3,4,5-bis(butyl-2-ene)tetrahydrofurfural (MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo, endo)-dimethyl bicyclo[2.2.1]hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; p-methane-3,8-diol, and normal-propyl N,N-diethylsuccinamate. Standard repellents for mosquitoes, ticks, and the like are citronella oil (discussed below), dimethyl phthalate, normal-butylmesityl oxide oxalate and 2-ethyl hexanediol-1,3 (See, Kirk-Othmer Encyclopedia of Chemical Technology, $2^{nd}$ Ed., Vol. 11: 724-728; and The Condensed Chemical Dictionary, $8^{th}$ Ed., p 756).

An insect repellent is any compound or composition that deters insects from a host. It will be appreciated that such usage makes no distinction among compounds that have highly ephemeral effects as compared to those that exhibit long-term beneficial effects, and/or those that require very high surface concentrations before there is an observable effect on insect behavior.

The term "insect repellent" thus indicates a compound or composition conferring on a host protection from insects when compared to no treatment at all. Protection desirably results in a statistically significant reduction in numbers of insects, and may, for example, be usefully determined by measuring mean complete protection time ("CPT") in tests in which insect behavior toward treated animals, including humans, and treated inanimate surfaces is observed. Mean CPT refers to the mean length of time over repetitions of tests in which the time before the first landing, probing or biting (in the case of a biting insect) or crawling (in the case of a crawling insect such as a tick or chigger) on a treated surface is observed [see e.g. US EPA Office of Prevention, Pesticides and Toxic Substances product performance test guidelines OPPTS 810.3700; and Fradin, M. S., Day, J. F. (2002) New England Journal of Medicine 347, 13-18]. In one exemplary embodiment of this invention, the insect repellent composition hereof has a mean CPT that is statistically indistinguishable from that of DEET. In the test in which this condition of the respective mean CPT performances of a DHN composition and DEET are shown to be statistically indistinguisable, the test conditions (including amounts of active ingredients) utilized must of course be identical, or, if not identical, must differ only in ways that do not prevent utilization of the results for the purposes of documenting the existence of the condition described.

As noted above, DHN compares favorably in performance with DEET. Moreover, DHN is advantageously prepared from naturally occurring nepetalactone derived from plants whereas DEET, and many other insect repellents, are not prepared from natural sources—an important consumer consideration when choosing an effective repellent. Preparation from natural sources also offers the potential for low production costs.

A useful property of DHN is that it provides a considerable improvement over the odor of DEET while exhibiting effective insect repellency. The DHN compounds and compositions of this invention possess a pleasant fragrance. The fragrance notes of the DHN materials make them useful in imparting, altering, augmenting or enhancing the overall olfactory component of an insect repellent composition or article, for example, by utilizing or moderating the olfactory reaction contributed by one or more other ingredients in the composition. Specifically, the DHN compositions of the invention may be utilized to either mask or modify the odor contributed by other ingredients in the formulation of the final repellent composition or article, and/or to enhance consumer appeal of a product by imparting a characteristic perfume or aroma.

In addition to the chemical compounds and compositions as described above, a variety of effective insect repellents contain essential oils and/or active ingredients of essential oils. "Essential oils" are defined as any class of volatile oils obtained from plants possessing the odor and other characteristic properties of the plant. Examples of repellent compounds that are essential oils include: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

In contrast to an insect repellent, an insecticide is a compound or mixture that is capable of poisoning an insect via its oral ingestion, by contact with the insect cuticle, or by fumigant action through the air. Thus, an insecticide is a type of pesticide designed to control insect life that is harmful to man (i.e., directly harmful as disease vectors, or indirectly harmful by destruction of crops, food products, or textile fabrics). Several well-known insecticides include: inorganic compounds (such as arsenic, lead and copper); naturally occurring organic compounds (such as rotenone, pyrethrins, nicotine, copper naphthenate and petroleum derivatives); and synthetic organic compounds (such as DDT, dieldrin, endrin, chlordane, lindane, para-dichlorobenzene and parathion).

A potentiated insect repellent composition is a repellent composition that produces a result substantially in excess of that which reasonably could be expected or predicted from the known effect of the components either alone or additively. In the present invention, a potentiated insect repellent composition will typically include dihydronepetalactones or a mixture thereof, and at least one other insect repellent compound that is not itself dihydronepetalactone (sometimes referred to as a non-dihydronepetalactone insect repellent compound).

An insect repellent composition can be used as a component of an insect repellent article, wherein an insect repellent article is an article of manufacture possessing insect repellency that is enhanced, altered, or augmented by the presence thereon or therein of an insect repellent composition. As used herein with respect to insect repellency, the terms "alter" and "modify" in their various forms refer to a means of supplying or imparting insect repellency to a composition, or augmenting the existing insect repellency characteristics where natural repellency is deficient in some regard, or supplementing the existing insect repellency to modify its quality, or character. The term "enhance" is intended to mean the intensification (without effecting a change in kind or quality of repellency) of one or more repellency properties in an insect repellent composition or insect repellent article.

The dihydronepetalactones of the present invention possess unique properties of insect repellency and are particularly effective against a wide spectra of common insect pests, including biting insects, wood-boring insects, noxious insects, and household-pests, and other insects that interfere with human society. These insects include a variety of biting insects (e.g., ants, bees, black flies, chiggers, fleas, green head flies, mosquitoes, stable flies, ticks, wasps, horn flies), wood-boring insects (e.g., termites), noxious insects (e.g., houseflies, cockroaches, lice, roaches, wood lice), and household pests (e.g., flour and bean beetles, dust mites, moths, silverfish, weevils). In the case of mosquitoes, which convey pathogenic microbes, these repellent properties are additionally effective for preventing infection with such diseases.

One property that is important to overall insect repellency is surface activity, as most (if not all) repellents contain both polar and non-polar regions in their structure. A second property is volatility. Insect repellents form an unusual class of compounds where evaporation of the active ingredient from the host's skin surface or from the insect repellent article is necessary for effectiveness, as measured by the host's protection from insect bites or the article's protection from insect damage. In the case of a topical insect repellent, a certain minimum concentration of repellent is needed in the air space directly above the skin surface of the host in order to repel insects, and this concentration is a measure of the potency of the repellent. However, evaporation rate is also affected by the rate of skin absorption—in most cases, penetration into and through the skin is an undesirable mode of loss of compound from the skin surface. Similar considerations must be made for insect repellent articles, concerning the minimum concentration of repellent required in the three-dimensional air space surrounding the article itself.

A variety of strategies are available to researchers attempting to balance these properties of evaporation (and, optionally, penetration). First, it is possible to find a single active ingredient having the right balance of physical properties. Alternatively, the active ingredient could be formulated with polymers and inert ingredients added to the active ingredient for the purpose of modifying the persistence of the active ingredient on the host's skin surface or within the insect repellent article. However, adding inert ingredients to the active ingredient limits the number of molecules of active ingredient on the surface of the repellent film or article. Since a molecule must be on the surface in order to evaporate, the evaporation rate is lowered. This carries with it the negative consequence of diluting the concentration of active ingredient that can be applied to the host's skin surface or that is present on the surface of an insect repellent article. This, in turn, reduces the overall potency of a formulation containing inert ingredients. In a third alternative, the active ingredient can be contained in microcapsules to control rates of loss from the host's skin surface or insect repellent article. Finally, another technique of limiting the evaporation rate of active ingredient is to synthesize a precursor molecule, which slowly disintegrates on the skin surface or insect repellent article to release the active ingredient.

For example, release of the active ingredient may be, for example, by sub-micron encapsulation, in which the active ingredient is encapsulated (surrounded) within a skin nourishing protein just the way air is captured within a balloon. The protein may be used at, for example, a 20% concentration. An application of repellent contains many of these protein capsules that are suspended in either a water-based lotion, or water for spray application. After contact with skin the protein capsules begin to breakdown releasing the encapsulated dihydronepetalactone. The process continues as each microscopic capsule is depleted then replaced in succession by a new capsule that contacts the skin and releases its active ingredient. The process may take up to 24 hours for one application. Because protein's adherence to the skin is so effective, these formulas are very resistant to perspiration (sweat-off), and water. When applied they are dry and comfortable with no greasiness. This system results in very effective protection, but it is only effective when used on skin because clothing does not have the capability to release the proteins. An alternative system uses a polymer to encase the repellent, which slows down early evaporation leaving more dihydronepetalactone available for later evaporation. This system can often increase a repellent's length of effectiveness by 25% to 50% over comparable non-entrapped products, but often feels greasy because of the presence of the polymer. In another alternative, a synergist is used to keep stimulating the evaporation of the dihydronepetalactone in the composition.

Regardless of the particular strategy applied to control volatility of an insect repellent, each repellent must have a minimum effective evaporation rate (MEER) from the skin surface or insect repellent article to maintain the necessary minimum concentration of repellent in the air space directly above the skin surface/article for effective insect repellency. An evaporation rate greater than the minimum effective evaporation rate (MEER) results in a significant and undesirable mode of loss. The issue is further complicated, however, since the MEER will change as a function of conditions in the field. Both the avidity or biting tendency of an insect and the concentration of insects in the host's environment must be considered. For example, as the avidity of mosquitoes increases, a higher MEER will be required. In an environment having a low concentration of mosquitoes where those mosquitoes are not hungry, the MEER could be as low as 2, or more commonly, 5 or 6. In contrast, in an environment having a high concentration of hungry mosquitoes, the MEER might be as high as 12-15. Preferred in the present invention are insect compositions wherein the skin surface evaporation rate is at least equal to a minimum effective evaporation rate over a period of time where a preferred period of time is about 5 hours.

The effectiveness of DHN or any insect repellent depends upon the surface concentration of the active ingredient on the host surface to which it is applied. Many compounds known in the art to exhibit insect repellency do so, however, only in relatively concentrated form. See, for example, McGovern et al in U.S. Pat. No. 4,416,881, which discloses the use of repellent concentrations of 6.25-25%. In other situations representative of the art, it is often found that concentrations of DEET much below 1% require repeated application to achieve an effective surface concentration, yet concentrations above 30% result in excessive surface concentration, which is both wasteful and conducive to the production of undesirable side effects. A further advantage of this invention is consequently that DHN not only provides effective insect repellency at concentrations similar to those employed for DEET, DHN may be employed at concentrations up to and including neat DHN (i.e. the composition hereof may, if desired, contain 100% by weight DHN). The property of effective repellency in DHN provides many options for economical utilization of the DHN active ingredient over a wide range of levels of concentration.

In one embodiment of this invention, DHN is incorporated in effective amounts into a composition suitable for application to a host plant or animal, preferably to human skin. Suitable compositions include DHN and a vehicle or a carrier, preferably an alcohol such as iso-propyl alcohol, a lotion such as one of the numerous skin creams known in the art, or a silicaceous clay. Preferably the DHN is present in the insect repellent composition of the invention at a concentration of about 0.1% to 30% by weight, preferably about 0.5% to 20% by weight, and most preferably about 1% to 15% by weight.

In this invention, a variety of carriers or diluents for the above-disclosed dihydronepetalactones can be used. The carrier allows the formulation to be adjusted to an effective concentration of repellant molecules. When formulating a topical insect repellent, preferably, the repellant molecules are mixed in a dermatologically acceptable carrier. The carrier may further provide water repellency, prevent skin irritation, and/or soothe and condition skin. Factors to consider when selecting a carrier(s) for any formulation of insect repellent include commercial availability, cost, repellency, evaporation rate, odor, and stability. Some carriers can themselves have repellent properties.

For the present invention, the specific choice of a carrier, if any, to be utilized in achieving the desired intimate admixture with the final product can be any carrier conventionally used in insect repellent formulations. The carrier, moreover, should preferably also be one that will not be harmful to the environment. Accordingly, the carrier can be any one of a variety of commercially available organic and inorganic liquid, solid, or semi-solid carriers or carrier formulations usable in formulating insect repellent products. For example the carrier may include silicone, petrolatum, lanolin or many of several other well-known carrier components.

Examples of organic liquid carriers include liquid aliphatic hydrocarbons (e.g., pentane, hexane, heptane, nonane, decane and their analogs) and liquid aromatic hydrocarbons. Examples of other liquid hydrocarbons include oils produced by the distillation of coal and the distillation of various types and grades of petrochemical stocks, including kerosene oils, which are obtained by fractional distillation of petroleum. Other petroleum oils include those generally referred to as agricultural spray oils (e.g., the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials.

Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g., tert-butyl sulfinyl dimethyl dithiocarbonate) can be used in conjunction with, or as a component of, the carrier or carriers comprising the compositions of this invention.

Solid carriers, which can be used in the compositions of the present invention include finely divided organic and inorganic solid materials. Suitable finely divided solid inorganic carriers include siliceous minerals such as synthetic and natural clay, bentonite, attapulgite, fuller's earth, diatomaceous earth, kaolin, mica, talc, finely divided quartz, and the like, as well as synthetically prepared siliceous materials, such as silica aerogels and precipitated and fume silicas. Examples of finely divided solid organic materials include cellulose, sawdust, synthetic organic polymers, and the like. Examples of semi-solid or colloidal carriers include waxy solids, gels (such as petroleum jelly), lanolin, and the like, and mixtures of well-known liquid and solid substances which can provide semi-solid carrier products, for providing effective repellency within the scope of the instant invention.

Other carriers suitable for use in a composition of this invention, in addition to water, include one or more of the following:

Acetone
C10~C18 Triglycerides
C12~C18 Acid Triglycerides
Dipropyl, Dibutyl, Diisocetyl, Diisopropyl or Dimethyl Oxalate
Cyclo(ethoxy)methicone
Amyl, Methyl, Butyl, Ethyl, Ethoxyethanol, Ethoxydiglycol or Tetrahydrofurfuryl Acetate
Ethoxydiglycol
Kerosene
Ethoxyethanol
Diacetin
Benzyl, Diacetone, Denatured ethyl, Tetrahydrofurfuryl or Oleyl Alcohol
Benzyl Benzoate or Laurate
Ethylene Carbonate
Ethyl Hexanediol
Oil of *Bertholetta Excelsa* Nut, *Carthamus Tinctorius, Helianthus Annuus, Ricinus Communis, Aleurites Moluccana, Linum Usitatissimum, Cocos Nucifera, Zea Mays, Pinus Palustris, Sesamum Indicum, Glycine Soja, Helianthus Annuus, Prunus Amygdalus Dulcis, Olea Europaea, Elaeis Guineensis, Prunus Persica Kernel, Cucurbita Pepo, Brassica Campestris, Oryza Sativa, Oryza Saliva, Carthamus Tinctorius, Juglans Regia* or *Triicum Vulgare*
Dibutyl Phthalate or Sebacate
Furfural
Butoxy-diglycol, -propanol or -ethanol
Diethoxyethyl Succinate
Diethyl Oxalate, Phthalate, Sebacate or Succinate
n- or t-Butyl, Hexyl or Isopropyl Alcohol
Glycofurol
Gycol
Butylene, Hexylene, Diethylene, Dipropylene, Pentylene, Propylene or Triethylene Glycol
C6~C20 linear, branched or cyclic alkane, alkanol or alkane polyol
Butyloctanol
Dihexyl, Diisobutyl, Diisodecyl, Ditridecyl, Dibutyl, Diisocetyl, Diisopropyl, Dipropyl or Diisoponyl Adipate
Butyrolactone
1,2,6-Hexanedol
Caprylic, Capric, Lauric or Stearic Triglyceride
Isoamyl, Isobutyl, Isopropy or Propyl Acetate
Isobutoxypropanol
Diisopropyl Sebacate
Dimethoxydiglycol
Isobutyl, Methyl or Stearyl Benzoate
Isopropyl Laurate, Myristate, Palmitate or Stearate
Octyl, Lauryl, Myristyl, Palmitoyl or Stearyl Benzoate
Dimethyl Phthalate, Glutarate, Maleate, Adipate or Succinate
Dimethyl Sulfone
Dimethyl Ether
Dimethyl Isosorbide
Dioctyl Sebacate, Adipale, Phthalate or Succinate
Methylethylketone
3-Methoxybutanol
Dipentene
Methoxydigycol
Diphenyl Methane
Methoxy-ethanol, -isopropanol or -methylbutanol
C4~C400 polyethylene, polypropylene, polyethylene/ether or polypropylene/ether glycol
perfluorodecalin
Methylal
Perfluorotetralin
Pheroxyisopropanol
Phenylpropanol
Methyl Hexyl Ether
Methylpropanediol
Methyl Pyrrolidone
Methyl Butyl Ketone
Thiolanediol
Toluene
Propanediol
Triacetin
Tributyl Citrate
Tributylcresylbutane
propylene Carbonate
Tricaprin
Tricaprylin
Trichloroethane
Triheptanoin
Trihydroxystearin
Triisononanoin
Tiisostearin
Trilaurin
Trilinolein
Trilinolenin
Trimethylhexanol
Trimyristin
Trioctanoin
Triolein
Tripalmitin
Trisebacin
Tristearin
Triundecanoin
Xytene In addition to the above-mentioned materials, such as the liquid hydrocarbons, the carrier can contain conventional emulsifying agents which can be used for causing the dihydronepetalactone compounds to be dispersed in, and diluted with, water for end-use application.

Insect repellent compositions of the present invention containing the dihydronepetalactones may also contain adjuvants known in the art of personal care product formulations, such as thickeners, buffering agents, chelating agents, preservatives, fragrances, antioxidants, gelling agents, stabilizers, surfactants, emolients, coloring agents, aloe vera, waxes, other penetration enhancers and mixtures thereof, and therapeutically or cosmetically active agents.

Additionally, the compositions of the present invention may also contain other adjuvants such as one or more therapeutically or cosmetically active ingredients. Exemplary therapeutic or cosmetically active ingredients useful in the compositions of the invention include fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents or antihistamines, and may be present in an amount effective for achieving the therapeutic or cosmetic result desired.

Additionally, the compositions of this invention may contain one or more other additives such as an antioxidant, an emulsion stabilizer, a preservative, a propellant, an emollient, a sunscreen agent, a surfactant, an emulsifying agent, a solubilizing agent and/or an ultraviolet light absorber. Examples of materials that may function as such additives are set forth below.

The compositions of this invention may include one or more materials that may function as an antioxidant, such as reducing agents and free radical scavengers. Suitable materials that may function as an antioxidant include one or more of the following:

Acetyl Cysteine
Ascorbic Acid
Ascorbyl Palmitate or Stearate
t-Butyl Hydroquinone
cysteine
Diamylhydroquinone
Dicetyl, Dilauryl, Dimyristyl, Distearyl or Ditridecyl Thiodipropionate
Erythorbic Acid
2-Ethylhexyl, Lauryl, Myristyl, Palmitoyl or Stearyl 4-methoxycinnamate
Ethyl Ferulate
Ferulic Acid
Hydroquinone
p-Hydroxyanisole
Hydroxylamine Sulfate
Magnesium Ascorbate
Magnesium Ascorbyl Phosphate
Octyl Gallate
Octyl, Lauryl, Myristyl, Palmitoyl or Stearyl Salicylate
Octocrylene
Phloroglucinol
Polyethylene glycol ether of tocopherol
Potassium Ascorbyl Tocopheryl Phosphate
Potassium Sulfite
Propyl Gallate
Rutin
Sodium Ascorbate
Sodium Erythorbate
Sodium Sulfite
Sodium Thloglycolate
Sorbityl Furfural
Tertiary butyl 4-methoxy phenol
Thiodiglycol
Thiodiglycolamide
Thioglycolic Acid
Thiolactic Acid
Thiosalicylic Acid
Tocopherol
Tocopheryl Acetate
Tocopheryl Linoleate
Tocopheryl Nicotinate
Tocopheryl Succinate
Tris(Nonylpheny)Phosphite The compositions of this invention may also include one or more materials that may function as an emulsion stabilizer. These materials would not act as primary emulsifiers, but would prevent or reduce the coalescence of emulsified droplets. This could be accomplished, for example, by modifying the continuous or the disperse phase of the emulsion through electrical repulsion, from changes in viscosity, or from film formation on the droplet surface. Suitable materials that may function as an emulsion stabilizer include one or more of the following:

Cetyl Alcohol
Montmorillonite
Aluminum Caprylate, Stearate, Laurate, Palmitate, Lanolate or Myristate
$C_{15}$~$C_{18}$ Glycol
Dodecylhexadecanol
$H(OCH_2CH_2)_nOH$ where n=350 to 160,000
Pectin
Glucose Pentaacetate
Glycol Oleate, Palmitate, Stearate or Ricinoleate
(Alkyl)cellulose
Hydroxyalkyl (alkyl)cellulose
Calcium Laurate, Myristate or Stearate
$C_{10}$~$C_{50}$ alcohol such as cetyl, myristyl, stearyl, tallow or lauryl alcohol
Polyvinyl Acetate
Lanolin
Styrene/maleic anhydride copolymer
Xanthan gum The compositions of this invention may also include one or more materials that may function as a preservative, which would prevent or retard microbial growth and thus protect the composition (or products made therefrom) from spoilage or from inadvertent contamination by the consumer during use. Suitable materials that may function as a preservative include one or more of the following:

Ammonium Benzoate or Propionate
Chloroxy enol
Isobutylparaben
o, m or p-Cresol
Isodecylparaben
Benzoic Acid
Isopropyl Cresol, Paraben or Sorbate
Benzotriazole
Benzyl Alcohol
Magnesium Benzoate
Benzylparaben
Dehydroacetic Acid
Magnesium Propionate
5-Bromo-5-Nitro-1,3-Dioxane
Diazolidinyl Urea
Magnesium Salicylale
2-Bromo-2-Nitropropane-1,3-Diol
Dibromopropamidine Diisothionate
Butyl Benzoate
Dimethyl Hydroxymethyl Pyrazole
Butylparaben
Dimethylol Ethylene Thiourea
Calcium Benzoate, Salicylate, Sorbate, Paraben or Propionate
Dimethyl Oxazolidine
Methyl Hydroxyl Hydantoin
Methyldibromo Glutaronitrile
Methylisothiazolinone
Methylparaben
Ethylparaben
Chlorhexidine Diacetate, Digluconate or Dihydrochloride
Formaldehyde
Glutaral Glyoxal
Chloroacetamide
Hexamidine
Chlorobutanol
Hexamidine Diparaben
Phenol
p-Chloro-m-Cresol
Hexamidine Paraben
Octyl, Lauryl, Myristyl, Palmitoyl or Stearyl Salicylate
Octyl, Lauryl, Myristyl, Palmitoyl or Stearyl Benzoate
Octocrylene
Phenoxyethanol
Chlorophene
4Hydroxybenzoic Acid
Phenoxyethylparaben
P-Chlorophenol
Hydroxymethyl Dioxoazabicyclooctane
Phenoxyisopropanol
Chlorothymol
Imidazolidinyl Urea
Phenyl Benzoate
Phenyl Mercuric Acetate, Benzoate, Borate, Bromide or Chloride
Potassium Salicylate, Sorbate, Benzoate, Propylparaben, Butylparaben, Ethylparaben, Methylparaben, Paraben, Phenoxide, o-Phenylphenate or Propionate
Propionic Acid
Propyl Benzoate
Phenylparaben
Propylparaben
o-Phenylphenol.
Silver Borosilicate
Silver Magnesium Aluminum Phosphate
Sorbic Acid
Sodium Hydroxymethylglycinate, Methylparaben, Paraben, Phenolsulfonate, Phenoxide, o-Phenylphenate, Propionate, Propylparaben, Pyrithione, Salicylate, Sorbate, Benzoate, Butylparaben, p-Chloro-m-Cresol, Dehydroacetate, Ethylparaben, Formate or Hydroxymethane Sulfonate
Zinc Pyrithione The compositions of this invention may also include one or more materials that may function as a propellant, which are chemicals used for expelling products from pressurized containers (aerosols). The functionality of a propellant depends on its vapor pressure at ambient temperature and its compressibility. Liquids or gases can be used as propellants as long as the pressure developed within the container is safely below the container's bursting pressure under normal storage and use conditions. Suitable materials that may function as a propellant include one or more of the following:

Butane
$CH_3CClF_2$
Nitrogen
Carbon Dioxide
$CH_3CF_2$
Nitrous Oxide
Dimethyl Ether
Isobutane
Pentane
Ethane
Isopentane
Propane
$CH_3CHF_2$ The compositions of this invention may also include one or more materials that may function as an emollient, which is a cosmetic ingredient that maintains the soft, smooth, and pliable appearance of skin. The purpose of an emollient is to remain on the skin surface or in the stratum corneum to act as a lubricant, to reduce flaking, and to improve the skin's appearance. Suitable materials that may function as an emollient include one or more of the following:

Acetylated Lanolin or Lanolin Alcohol
Bisphenylhexamethicone
*Bertholetta Excelsa* Nut Oil
Caprylic/Capric Glycerides
Butoxyethyl Stearate
Caprylic/Capric/Succinic Triglyceride
Acetylated Sucrose Distearate
Acetyl Trihexyl Citrate
Butyl Isostearate, Myristate, Oleate or Stearate
caprylyl Glycol
Acetyl Trioctyl Citrate
Cetearyl Octanoate or Palmitate
*Prunus Armenlaca* Kernel Oil
Cetyl Acetate, Caprylate, Lactate, Laurate, Octanoate or Oleate
Arachidyl Propionate
$C14$–$C15$ Alcohols
Cetylarachidol
*Argania Spinosa* Oil
$C12$–$C28$ Alkyl Acetate, Benzoate or Lactate or Octanoate
*Persea Gratissima* Oil
*Orbignya Olelfera* Oil
*Melissa Officinalis* Seed Oil
$C24$–$C28$ Alkyl Methicone
$C12$–$C13$ Alkyl Octanoate
Cetyl Glycol, Glycol Isostearate or Glycol Palmitate
Benzyl Laurate
Bis-Diglyceryl Polyacyladipate-1 or -2
*Camellia Kissi* Oil
Isostearyl, Myristyl, Lauryl, Isocetyl, Pentadecyl, Oleyl, Tridecyl or Undecyl Alcohol
Isostearyl Glyceryl Ether
Isostearyl Benzoate, Lactate, Neopentanoate, Octanoate, Palmitate or Myristate
Methyl Stearate
*Rosa Moschata* Seed Oil
Hydroxycetylisostearate
*Isatis Tinctoria* Oil
Isoamyl Laurate
Isobutyl Myristate, Palmitate, Pelargonate or Stearate
Isopropyl Laurate, Myristate, Palmitate or Stearate
Isotridecyl Isononanoate
Myristyl Isostearate, Lactate, Neopentanoate, Octanoate or Propionate
*Actinidia Chinensis* Seed Oil
Isocetyl Isodecanoate, Palmitate or Stearate
Lanolin
Lanolin Oil or Wax
Isodecyl Citrate, Hydroxystearate, Laurate, Myristate, Neopentanoate, Palmitate or Stearate
Neopentyl Glycol Dicaprylate, Dicaprate, Dilaurate or Dioctanoate
Nonyl Acetate
Lauryl Glycol
Octyl Acetoxystearate
Lauryl Isostearate or Lactate
Octyldecanol
Octyldodecanol
Octyldodecyl Benzoate, Lactate, Neopentanoate or Octanoate
Octyl, Lauryl, Myristyl, Palmitoyl or Stearyl Benzoate
Isohexadecane Methyl Benzoate, Caproate, Caprylate, Caprate or Glucose Dioleate
Isohexyl Neopentanoate, Palmitate or Laurate
Octyl Hydroxystearate, Laurate, Isopalmitate, Isostearate, Myristate, Neopentanoate, Oleate, Palmitate or Stearate
Methyl Glucose Isostearate, Laurate, Sesquicaprylate, Sesquicaprate, Sesquilaurate or Sesquistearate
Isopropyl Hydroxycetyl Ether
Isopropyl Hydroxystearate, Isostearate, Lanolate, Laurate, Linoleate, Myristate or Oleate
2-Oleamido-1,3-Octadecanediol
Oleyl Acetate, Lactate or Oleate
Methyl Hydroxystearate, Laurate, Isostearate, Myristate, Oleate, Palmitate or Pelargonate
Isopropyl Palmitate, Isopropyl or Stearate
Isosorbide Laurate
*Passiflora Eduls* Oil
Polyethyelene Glycol Glycerides
Polyglyceryl Myristate, Oleate, Pentastearate or Ricinoleate
Polyglyceryl Oleyl Ether
Polyethylene Glycol Tricapryl Citrate, Tricetyl Citrate, Trilauryl Citrate, Trimyristyl Citrate or Tristearyl Citrate
Polyethylene Glycol Castor Oil
Pentaerythrityl Dioleate, Distearate, Stearate, Tetrabenzoate or Trioleate
Polyglyceryl Sesquioleate, Stearate, Tetraoleate, Tetrastearate, Caprate, Caprylate, Decalinoleate, Laurate or Isopalmitate
Propylene Glycol Hydroxystearate Stearate, Laurate, Linoleate, Myristate, Ricinoleate, Stearte, Oleate, Soyate or Caprylate
Propylene Glycol Myristyl Ether or Myristyl Ether Acetate
Sucrose Polyoleate, Polypalmate, Polystearate, Ricinoleate, Stearate, Triacetate, Polylaurate, Polylinoleate, Myristate, Oleate, Laurate or Palmitate
Polypropylene Glycol Lauryl, Cetyl, Stearyl, Oleyl or Pentaerythrityl Ether
Tridecyl Neopentanoate, Octanoate, Stearate or Isononanoate
Stearyl Acetate, Benzoate or Lactate
Stearyl Glycol Isostearate or Citrate
Polypropylene Glycol/Polyethylene Glycol
Trimethylolpropane or Propene
Trioctyl Trimellitate
Tris(Tributoxysiloxy)Methylsilane The compositions of this invention may also include one or more materials that may function as a sunscreen agent. Under 58 Fed. Reg. 28194 (May 12, 1993), a sunscreen active ingredient is defined as an "ingredient that absorbs at least 85 percent of the radiation in the UV range at wavelengths from 290 to 320 nanometers, but may or may not transmit radiation at wavelengths longer than 320 nanometers." Suitable materials that may function as a sunscreen agent include one or more of the following:

Aminobenzoic Acid ("PABA")
Glyceryl Aminobenzoate (Glyceryl PABA)
Oxybenzone (Benzophenone-3)
Cinoxate
Homosalate
Octyl Dimethyl PABA
Diethanolamine Methoxycinnamate
2-Ethylhexyl, Lauryl, Myristyl, Palmitoyl, or Stearyl 4-methoxycinnamate
Lawsone with Dihydroxyacetone
Phenylbenzimidazole Sulfonic Acid
Menthyl Anthranilate
Red Petrolatum
Digalloyl Trioleate
Octocrylene
Sulisobenzone (Benzophenone-4)
Dioxybenzone (Benzophenone-8)
Octyl Methoxycinnamate
Titanium Dioxide
Ethyl 4-[bis(Hydroxypropyl)]Aminobenzoate(Ethyl Dihydroxypropyl PABA)
Octyl Salicylate
Trolamine Salicylate The compositions of this invention may also include one or more materials that may function as a surfactant, an emulsifying agent or a solubilizing agent. Such a material may be used to reduce surface tension, to form complex films on the surface of emulsified droplets, to create a repulsive barrier on emulsified droplets to prevent their coalescence, to retard physical changes in emulsions throughout during shelf-life or to cause a solute to become part of a micelle formed by a surfactant. Suitable materials that may function as a surfactant, an emulsifying agent or a solubilizing agent include one or more of the following:

C50~C650 linear or branched dihydroxy polyoxyethylene/polyoxypropylene block copolymer
C50~C650 branched polyhydroxy polyoxyethylene/polyoxypropylene block copolymer of ethylene diamine
C12~C330 ethoxylated alkyl phenol
C16~C140 polyethylene glycol ether of C12~C60 alcohols
Carboxylic acid esters of C12~C330 ethoxylated alkyl phenol
Ester of C12~C40 Carboxlic Acid and C8~C40 Polyethylene Glycol
Ester of Caprylic or Capric Triglyceride and C8~C40 Polyethylene Glycol
Phosphoric acid esters of C12~C330 ethoxylated alkyl phenol
Phosphoric acid esters and diesters of C16~C140 polyethylene glycol ether of C12~C60 alcohols
Abietic Acid
Calcium Stearoyl Lactylate
Cetethyl Morpholinium Ethosutfate
Cetrimonium Bromide, Chloride, Methosulfate or Tosylate
Cetyl Alcohol
cetyl Dimethicone Copolyol
Cetyl Glyceryl Ether/Glycerin Copolymer
Cetyl Phosphate
Cetearyl Glucoside
Dextrin Behenate, Laurate, Myristate, Palmitate or Stearate
Dicetyl Phosphate
Diethytaminoethyl Laurate or Stearate
Dimethyl Octynediol
Dimyristyl Phosphate
Glyceryl Arachidate, Behenate, Caprylate, Caprate, Cocoate, Erucate, Hydrogenated Rosinate, Hydroxystearate, Isopalmitate, Isostearate, Isotridecanoate/Stearate/Adipate, Lanolate, Laurate, Oleate, Linoleate, Linolenate, Oleate, Montanate, Myristate, Palmitate, Stearate, Palmitoleate, Ricinoleate or Uridecylenate
Glycol Octanoate
Hydrogenated Lecithin
Hydrogenated Palm Glyceride
Hydroxycetyl Phosphate
Hydroxyethyl Glyceryl Oleate and/or Stearate
Lanolin
Laurtrimonium Chloride Lauryl Phosphate
Lecithin
Mannitan Laurate or Oleate
Myristoyl Methylalanine
Palmitic Acid
Octoxyglyceryl Behenate or Palmitate
Pelargonic Acid
Pentaerythrityl Stearate
Phosphatidylcholine
Potassium Laurate, Myristate, Oleate, Lauryl Hydroxypropyl Sulfonate, Cetyl Phosphate, Lauryl Sulfate, Palmate, Palmitate, Ricinoleate or Stearate
Sodium Palmate, Palmitate, Phthalate Stearyl Amide, Ricinoleate, Stearate, Stearyl Sulfate, Trideceth Sulfate, Tridecyl Sulfate, Undecylenate, Lauroyl Lactylate, Lauryl Phosphate, Myristate, Oleate, Oleoyl Lactylate, Behenoyl Lactylate, Caproyl Lactylate, Caprylate, Isostearoyl Lactylate or Laurate
Propylene Glycol Behenate, Caprylate, Hydroxystearate, Isostearate, Laurate, Linoleate, Unolenate, Myristate, Oleate, Ricinoleate or Stearate
Sorbitan Caprylate, Diisostearate, Dioleate, Distearate, Isostearate, Laurate, Oleate, Palmitate, Sesquiisostearate, Sesquioleate, Sesquistearate, Stearate, Triisostearate, Trioleate or Tristearate
Raffinose Oleate
Stearic Acid
Stearoyl Lactylic Acid
Stearyl Alcohol
Sucrose Dilaurate, Distearate, Laurate, Myristate, Oleate, Palmitate, Polylaurate, Polylinoleate, Polyoleate, Polypalmate or Polystearate
$C32{\sim}C82$ polyethylene glycol ether of behenyl alcohol
$C20{\sim}C106$ polyethylene glycol ether of cetyl alcohol
$C28{\sim}C80$ polyethylene glycol ether of cetyl or oleyl alcohol
$C20{\sim}C70$ polyethylene glycol ether of cetyl and/or stearyl alcohol
$C20{\sim}C80$ polyethylene glycol ether of cholesterol
$C16{\sim}C24$ polyethylene glycol ether of decyl alcohol
$C40{\sim}C80$ polyethylene glycol ether of dihydrocholesterol
$C20{\sim}C60$ polyethylene glycol ether of isocetyl alcohol
$C18{\sim}C30$ polyethylene glycol ether of isodecyl alcohol
$C18{\sim}C40$ polyethylene glycol ether of isolauryl alcohol
$C20{\sim}C120$ polyethylene glycol ether of isostearyl alcohol
$C12{\sim}C120$ polyethylene glycol ether of glyceril caprate, caprylate, laurate, myristate, oleate, palmitate or stearate
$C14{\sim}C100$ polyethylene glycol ether of lauryl alcohol
$C16{\sim}C24$ polyethylene glycol ether of myristyl alcohol
$C20{\sim}C70$ polyethylene glycol ether of oleyl alcohol
$C10{\sim}C100$ polyethylene/polypropylene glycol ether of butyl alcohol
$C20{\sim}C106$ polyethylene/polypropylene glycol ether of cetyl alcohol
$C20{\sim}C100$ polyethylene/polypropylene glycol ether of decyl alcohol
$C14{\sim}C100$ polyethylene/polypropylene glycol ether of lauryl alcohol
carboxylic acid ester of $C20{\sim}C120$ polyethylene glycol ether of isostearyl alcohol
Carboxylic acid esters of $C14{\sim}C100$ polyethylene glycol ether of lauryl alcohol
Carboxylic acid ester of $C16{\sim}C24$ polyethylene glycol ether of myristyl alcohol
Citric acid diesters of $C14{\sim}C100$ polyethylene glycol ether of lauryl alcohol
Isopropyl Laurate, Myristate, Palmitate or Stearate
Lauric acid ester of $C30{\sim}C120$ polyethylene glycol ether of sorbitol
Octyl, Lauryl, Myristyl, Palmitoyl or Stearyl Salicylate
Phosphoric acid ester of $C20{\sim}C106$ polyethylene glycol ether of cetyl alcohol
Phosphoric acid ester of $C20{\sim}C120$ polyethylene glycol ether of isostearyl alcohol
Phosphoric acid diesters of $C14{\sim}C100$ polyethylene glycol ether of lauryl alcohol
Phosphoric acid esters and/or diesters of $C20{\sim}C70$ polyethylene glycol ether of oleyl alcohol
Stearic acid ester of $C15{\sim}C30$ polyethylene glycol ether of glycerin
Stearic acid ester of $C20{\sim}C60$ polyethylene glycol ether of isocetyl alcohol
Stearic acid ester of $C20{\sim}C120$ polyethylene glycol ether of isostearyl alcohol
Diethanolamine salt of phosphoric acid ester of $C20{\sim}C106$ polyethylene glycol ether of cetyl alcohol
Diethanolamine salt of phosphoric acid ester of $C20{\sim}C70$ polyethylene glycol ether of cetyl and/or stearyl alcohol
Diethanolamine salt of Phosphoric acid ester of $C20{\sim}C70$ polyethylene glycol ether of oleyl alcohol
Disodium salt of citric acid ester of $C14{\sim}C100$ polyethylene glycol ether of lauryl alcohol
Disodium salt of phosphoric acid ester of $C14{\sim}C100$ polyethylene glycol ether of lauryl alcohol
Disodium salt of phosphoric acid ester of $C20{\sim}C70$ polyethylene glycol ether of oleyl alcohol
Monoethanolamine salt of phosphoric acid ester of $C20{\sim}C70$ polyethylene glycol ether of cetyl and/or stearyl alcohol
$C12{\sim}C120$ polyethylene glycol diester of behenic, capric, caprylic, lauric, oleic, octanoic, palmitic or stearic acid
Polyesters of $C6{\sim}C40$ polyglycerin and behenic, capric, caprylic, lauric, oleic, octanoic, palmitic or stearic acid.

The compositions of this invention may also include one or more materials that may function as an ultraviolet light absorber to protect a product made from the composition from chemical or physical deterioration induced by ultraviolet light. UV absorbers, like sunscreen agents, have the ability to convert incident ultraviolet radiation into less damaging infrared radiation (heat). Suitable materials that may function as an ultraviolet light absorber include one or more of the following:

Acetaminosalol
3-Benzylidene Camphor
Stilbenedisulfonate
Allantoin PABA
Disodium Distyrylbiphenyl Disulfonate
Benzalphthalide
Sulfonamide
Drometrizole
Benzophenone
Benzylidene Camphor Sulfonic Acid
Ethyl Dihydroxypropyl PABA
Benzophenone substituted with one or more groups selected from hydroxyl, alkoxy, alkyl, halogen and sulfonate
Benzyl Salicylate
Ethyl Diisopropylcinnamate, Methoxycinnamate or Urocanate
Bumetrizole
Ethyl PABA
Butyl Methoxydibenzoylmethane
Butyl PABA
Etocrylene Cinoxate
Ferulic Acid
Glyceryl Octanoate Dimethoxycinnamate
Di-t-Butyl Hydroxybenzylidene Camphor
Glyceryl PABA
Digalloyl Trioleate
Glycol Salicylate
Diisopropyl Methyl Cinnamate
Isoamyl p-Methoxycinnamate
Disodium Bisethylphenyl Triaminotriazine
Isopropylbenzyl Salicylate
Isopropyl Dibenzoylmethane
Octyl Triazone
Sodium Urocanate
Isopropyl Methoxycinnamate
PABA
Menthyl Anthranilate or Salicylate
pentyl Dimethyl PABA
Terephthaylidene Dicamphor Sulfonic Acid
4-Methylbenzylidene Camphor
Phenylbenzimidazole Sulfonic Acid
Titanium Dioxide
Octocrylene
Polyacrylamidomethyl Benzylidene Camphor
TriPABA Panthenol
Octrizole
Potassium Methoxycinnamate
Urocanic Acid
Octyl Dimethyl PABA
Potassium Phenylbenzimidazole Sulfonate
Octyl Methoxycinnamate or Salicylate
Sodium Phenylbenzimidazole Sulfonate A formulated mixture of one or more carriers, adjuvants and/or additives may be selected from the members of the groups thereof contained in the lists set forth above. They may also be selected from a subgroup of the members of the foregoing lists formed by omitting any one or more members from the whole groups as set forth in the above lists. As a result, a mixture of carriers, adjuvants and/or additives may in such instance not only be made from one or more members selected from any subgroup of any size that may be formed by all the various different combinations of individual members from the whole groups as set forth in the above lists, but may also be made in the absence of members that have been omitted from the whole groups to form the subgroup. The subgroup formed by omitting various members from the whole group in the list above may, moreover, be an individual member of a whole group such that a carrier, adjuvant and/or additive is provided in the absence of all other members of the whole groups except the selected individual member.

Dihydronepetalactones may be utilized in the present invention individually or combined in any proportion. As is conventional in the art, the desired amount of an insect repellent composition to be added to a given insect susceptible article with properties of insect repellency is determined by the nature of the product and other factors. These factors include both considerations of cost and the nature of the other ingredients in the insect repellent composition or repellent article, their amounts, and the desired repellency effect. In general, the composition of the repellent should contain sufficient amounts of active insect repellant material to be efficacious in repelling the insect from the host over a prolonged period of time (preferably, for a period of at least several hours).

The amount of each dihydronepetalactone of Formula I or mixtures thereof in an insect repellent composition or repellent article that contains one or more of the carriers, adjuvants and/or additives as described above will generally not exceed about 80% by weight based on the weight of the final product, however, greater amounts may be utilized in certain applications and this amount is not limiting. More preferably, a suitable amount of dihydronepetalactone will be at least about 0.001% by weight and preferably about 0.01% up to about 50% by weight; and more preferably, from about 0.01% to about 20% weight percent, based on the weight of the composition or article. Specific compositions will depend on the intended use.

The dihydronepetalactone repellent compositions of the present invention can be formulated without a carrier and be effective. More often, however, the insect repellent composition will include a carrier and contain about 0.001-50% weight of the disclosed compounds, and such compound is usually in intimate mixture with the carrier to bring the active material into position for repelling common insect pests, such as biting insects, wood-boring insects, noxious insects, household pests, and the like.

The compositions of the invention may be formulated and packaged so as to deliver the product in a variety of forms including as a solution, suspension, cream, ointment, gel, film or spray, depending on the preferred method of use. The carrier may be an aerosol composition adapted to disperse the dihydronepetalactone into the atmosphere by means of a compressed gas.

Desirable properties of a topical insect repellent article include low toxicity, resistance to loss by water immersion or sweating, low or no odor or at least. a pleasant odor, ease of application, and rapid formation of a dry tack-free surface film on the host's skin. In order to obtain these properties, the formulation for a topical insect repellent article should permit insect-infested animals (e.g., dogs with fleas, poultry with lice, cows with ticks, and humans) to be treated with an insect repellent composition of the present invention by contacting the skin, fur or feathers of such an animal with an effective amount of the repellent article for repelling the insect from the animal host. Thus, dispersing the article into the air or dispersing the composition as a liquid mist or fine dust will permit the repellent composition to fall on the desired host surfaces. Likewise, directly spreading of the liquid/semi-solid/solid repellent article on the host is an effective method of contacting the surface of the host with an effective amount of the repellent composition.

Embodiments of the present invention which may be used as a topical insect repellent articles, include (but are not limited to): colognes, lotions, sprays, creams, gels, ointments, bath and shower gels, foam products (e.g., shaving foams), makeup, deodorants, shampoo, hair lacquers/hair rinses, and personal soap compositions (e.g., hand soaps and bath/shower soaps).

This invention also relates to the use of dihydronepetalactone mixtures as insect repellents in a variety of articles, which are susceptible to attack by insects. These outdoor consumable products will generally, but not necessarily, comprise an insect repellent composition of the invention, but will contain an effective amount of dihydronepetalactone. Typical articles that can be improved by the use of dihydronepetalactones and mixtures thereof include, but are not limited to: air fresheners, candles, other scented articles, fibers, sheets, cloth [e.g., for clothing, nettings (mosquito netting), and other fabrics], paper, paint, ink, clay, woods, furniture (e.g., for patios and decks), carpets, sanitary goods, plastics, polymers, and the like.

The dihydronepetalactone compositions of this invention may be blended with polymers, which may also involve a controlled release systems. Compatible polymers may or may not be biodegradable. Exemplary polymers are high-density polyethylene or low-density polyethylene, biodegradable thermoplastic polyurethanes, biodegradable ethylene polymers, and poly(epsilon caprolactone) homopolymers and compositions containing the same as disclosed in U.S. Pat. Nos. 4,496,467, 4,469,613 and 4,548,764.

Dihydronepetalactones are particularly advantageous for use as repellent materials in preparations of the present invention for a variety of reasons.

First, the compounds are cost effective to produce, an important consumer consideration when choosing an effective repellent. Many commercially available repellent products are only effective in relatively concentrated form, including as much as 5-30% (or more) repellent in a carrier, based on total weight. U.S. Pat. No. 4,416, 881 to McGovern et al., for example, discloses repellent concentrations of 6.25-25% repellent in a carrier.

Secondly, the compounds are known natural compounds, thus overcoming concerns raised against synthetic chemicals such as DEET as the primary active ingredient in repellent compositions.

Finally, in addition to the natural repellent properties of the dihydronepetalactone mixtures thus prepared, the compositions also possess a unique and pleasant fragrance. The fragrance notes of the subject compounds make them useful in imparting, altering, augmenting or enhancing the overall olfactory component of an insect repellent composition or article, for example, by utilizing or moderating the olfactory reaction contributed by one or more other ingredients in the composition. Specifically, the dihydronepetalactones of the invention or mixtures thereof may be utilized to either mask or modify the odor contributed by other ingredients in the formulation of the final repellent composition or article, and/or to enhance consumer appeal of a product by imparting a characteristic perfume or aroma. It is expected that the pleasant fragrance of dihydronepetalactones will possess much greater appeal to consumers than other insect repellent compounds, particularly DEET.

Dihydronepetalactones and their uses are also described in U.S. Ser. No. 10/349,865, filed Jan. 23, 2003, which is incorporated in its entirety as a part hereof for all purposes.

Where the composition of this invention is stated or described as comprising, including, containing, having, being composed of or being constituted by certain components, it is to be understood, unless the statement or description explicitly provides to the contrary, that one or more components in addition to those explicitly stated or described may be present in the composition. In an alternative embodiment, however, the composition of this invention may be stated or described as consisting essentially of certain components, in which embodiment components that would materially alter the principle of operation or the distinguishing characteristics of the composition are not present therein. In a further alternative embodiment, the composition of this invention may be stated or described as consisting of certain components, in which embodiment components other than impurities are not present therein.

Where the indefinite article "a" or "an" is used with respect to a statement or description of the presence of a component in the composition of this invention, it is to be understood, unless the statement or description explicitly provides to the contrary, that the use of such indefinite article does not limit the presence of the component in the composition to one in number.

What is claimed is:

1. A sprayable insect repellent composition comprising a component (a) that comprises a dihydronepetalactone, or a mixture of dihydronepetalactone stereoisomers, as set forth by the formula:

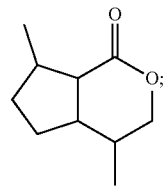

a component (b) that comprises an aliphatic alcohol;
a component (c) that comprises a mixture of
  (i) one or more members of the group consisting of (AI) cyclo(ethoxy) methicone, (BI) bisphenyl hexamethicone, (CI) $C_{24}$~$C_{28}$ alkyl methicone, and (DI) cetyl dimethicone polyol;
  (ii) one or more members of the group consisting of (AII) glycol ricinoleate, (BII) polyglyceryl ricinoleate, (CII) propylene glycol ricinoleate, and (DII) glyceryl ricinoleate; and
  (iii) octyldodecanol;
a component (d) that comprises a $C_{50}$~$C_{650}$ branched polyhydroxy polyoxyethylene/polyoxypropylene block copolymer of ethylene diamine;
a component (e) that comprises
  (i) a mixture of butylene glycol, propylene glycol and methyl propanediol, and/or
  (ii) a mixture of glycerol, methyl propanediol and isostearyl neopentanoate; and
a component (f) that comprises one or more members of the group consisting of aminobenzoic acid, glyceryl aminobenzoic acid, oxybenzone, sulisobenzone, dioxybenzone and titanium dioxide.

2. The composition according to claim 1 wherein component (b) is selected from one or more members of the group consisting of methyl, ethyl, normal-propyl, isopropyl, normal-butyl, sec-butyl, and tert-butyl alcohol.

3. The composition according to claim 1 wherein component (c)(i) comprises cyclo(ethoxy) methicone.

4. The composition according to claim 1 wherein component (c)(i) comprises cetyl dimethicone polyol.

5. The composition according to claim 1 wherein component (c)(ii) comprises polyglyceryl ricinoleate.

6. The composition according to claim 1 wherein component (c)(ii) comprises propylene glycol ricinoleate.

7. The composition according to claim 1 wherein component (e) comprises both components (e)(i) and (e)(ii).

8. The composition according to claim 1 formulated as a liquid.

9. The composition according to claim 1 formulated as an aerosol.

* * * * *